(12) United States Patent
Mueller

(10) Patent No.: US 7,345,279 B2
(45) Date of Patent: Mar. 18, 2008

(54) IDENTIFICATION OF HIDDEN OBJECTS BY TERAHERTZ HETERODYNE LASER IMAGING

(75) Inventor: Eric R. Mueller, West Suffield, CT (US)

(73) Assignee: Coherent, Inc., Santa Clara, CA (US)

( * ) Notice: Subject to any disclaimer, the term of this patent is extended or adjusted under 35 U.S.C. 154(b) by 77 days.

(21) Appl. No.: 11/231,079

(22) Filed: Sep. 20, 2005

(65) Prior Publication Data
US 2007/0228280 A1    Oct. 4, 2007

(51) Int. Cl.
*G01J 5/02* (2006.01)
(52) U.S. Cl. .................................................. 250/341.1
(58) Field of Classification Search ............. 250/341.1
See application file for complete search history.

(56) References Cited

U.S. PATENT DOCUMENTS

| | | | |
|---|---|---|---|
| 4,084,158 A | 4/1978 | Slawsby | 342/25 F |
| 4,280,127 A | 7/1981 | Lee et al. | 342/25 A |
| 5,022,091 A | 6/1991 | Carlson | 382/240 |
| 5,936,237 A | 8/1999 | van der Weide | 250/234 |
| 5,969,662 A | 10/1999 | Hellsten | 342/25 A |
| 6,078,047 A | 6/2000 | Mittleman et al. | 250/338.1 |
| 6,150,972 A | 11/2000 | Bickel et al. | 342/25 C |
| 6,525,862 B2 | 2/2003 | Fisher et al. | 359/278 |
| 7,087,902 B2 | 8/2006 | Wang et al. | 250/341.1 |
| 2003/0178584 A1 | 9/2003 | Amone et al. | 250/495.1 |
| 2004/0061055 A1 | 4/2004 | Kawase et al. | 250/330 |
| 2004/0065831 A1 | 4/2004 | Federici et al. | 250/341.1 |
| 2004/0140924 A1 | 7/2004 | Keller et al. | 342/22 |
| 2004/0155665 A1 | 8/2004 | Amone et al. | 324/644 |
| 2004/0252024 A1 | 12/2004 | Huey et al. | 340/540 |
| 2004/0263379 A1 | 12/2004 | Keller | 342/22 |
| 2005/0023470 A1* | 2/2005 | Ferguson et al. | 250/358.1 |
| 2005/0230604 A1 | 10/2005 | Rowe et al. | 250/221 |
| 2005/0231415 A1 | 10/2005 | Fleisher et al. | 342/22 |
| 2005/0231421 A1 | 10/2005 | Fleisher et al | 342/179 |
| 2005/0232459 A1 | 10/2005 | Rowe et al. | 382/100 |
| 2005/0242287 A1 | 11/2005 | Hakimi | 250/363.09 |

(Continued)

FOREIGN PATENT DOCUMENTS

GB    2 359 716 A    8/2001

OTHER PUBLICATIONS

E.R. Mueller, "Frequency-Shifting Submillimeter Single-Sideband Receiver," *International Journal of Infrared and Millimeter Waves*, vol. 15, No. 4, 1994, pp. 665-670.

(Continued)

*Primary Examiner*—David Porta
*Assistant Examiner*—Mindy Vu
(74) *Attorney, Agent, or Firm*—Stallman & Pollock LLP

(57) ABSTRACT

A method for inspecting a package to identify an object concealed in the package includes passing two beams of THz-radiation through the package. The frequency of THz radiation in one beam is different from that in the other, and the beams are at an angle to each other. Each of the transmitted beams is used to form an image of the package and the object. The absorption coefficient of the object is determined from the two images. The material of the object is determined from the absorption coefficients at the two frequencies. The method is useful for detecting explosive material concealed in baggage.

20 Claims, 4 Drawing Sheets

U.S. PATENT DOCUMENTS

| | | | |
|---|---|---|---|
| 2006/0016997 A1 | 1/2006 | Siegel et al. | 250/339.11 |
| 2006/0022140 A1 | 2/2006 | Connelly et al. | 250/338.1 |
| 2006/0055936 A1 | 3/2006 | Yun et al. | 356/479 |
| 2006/0056586 A1 | 3/2006 | Uetake et al. | 378/57 |
| 2006/0104480 A1 | 5/2006 | Fleisher | 382/103 |
| 2006/0164287 A1 | 7/2006 | Holt et al. | 342/22 |
| 2006/0214107 A1 | 9/2006 | Mueller | 250/341.8 |
| 2006/0235621 A1 | 10/2006 | Cole et al. | 702/19 |
| 2006/0239404 A1 | 10/2006 | Udpa et al. | 378/62 |
| 2006/0255277 A1* | 11/2006 | Cole et al. | 250/341.1 |

OTHER PUBLICATIONS

F. Huang et al., "Noninvasive Study of Explosive Materials by Time Domain Spectroscopy and FTIR," *AIP Conference Proceedings*, vol. 760, Issue 1, Apr. 9, 2005, pp. 578-585

D.J. Cook et al. "Quantitative THz Spectroscopy of Explosive Materials," *Optical Society of America (PSI-SR-1196)*, Copyright 205, 4 pages in length.

F. Oliveira et al., "Analysis of Terahertz Spectral Images of Explosives and Bio-Agents Using Trained Neural Networks," *Proc. SPIE*, vol. 5411 (2004), pp. 1-6.

Powerpoint presentation by J.F Federici et al., "Terahertz Imaging and Detection of Suicide Bombers ," *NJIT Department of Physics*, Funded by US Army and NSF (2005), 16 pages in length.

Article, "Terahertz Scattering for Detection of Improvised Explosive and Bio-agent Dispersal Devices," *NEAR-LAB (Northwest Electromagnetic and Acoustics Research Laboratory*, printed Sep. 19, 2005, from http://nearlab.ece.pdx.edu/terahertz_ imaging.htm web site, 3 pages in length.

In re U.S Appl. No. 11/231,079, filed Sep. 20, 2005, By Eric Mueller, entitled "Identification of Hidden Objects by Terahertz Heterodyne Laser Imaging".

S. Wang et al., "Pulsed terahertz tomography," *Journal of Physics D: Applied Physics*, vol. 37, No. 4, Feb. 21, 2004, pp. R1-R36.

X.-C. Zhang, "Three-dimensional terahertz wave imaging," *Phil. Trans. R. Soc. Lond. A*, vol. 362 (2004), pp. 283-299.

S. Wang et al., "Tomographic imaging with a terahertz binary lens," *Applied Physics Letters*, vol. 82, No. 12, Mar. 24, 2003, pp. 1821-1823.

\* cited by examiner

IDENTIFICATION OF HIDDEN OBJECTS BY TERAHERTZ HETERODYNE LASER IMAGING

TECHNICAL FIELD OF THE INVENTION

The present invention relates in general to terahertz (THz) lasers. The invention relates in particular to identifying objects in a container by transmitting radiation from two THz-lasers through the container.

DISCUSSION OF BACKGROUND ART

The terahertz frequency spectral range is a relatively underdeveloped band of the electromagnetic spectrum. The terahertz band is bordered by the infrared on the short-wavelength side and millimeter-waves on the long-wavelength side. The terahertz band encompasses radiation having a frequency range of 0.3 to 10.0 THz and wavelengths between about 30 micrometers ($\mu$m) and 1 millimeter (mm). The terahertz band is sometimes referred to by practitioners of the art as the far infrared (FIR).

Many materials that are opaque to wavelengths shorter then 30 micrometers are either transparent or semi-transparent in the terahertz band. Such materials include plastic, textiles, paper, cardboard, wood, ceramics, opaque glasses, semiconductors, and the like. Radiation at longer wavelengths, for example, millimeter waves have better transmissivity than terahertz radiation in these materials but the longer wavelengths are unsuitable for use in high resolution imaging systems. Further, such materials do not have much spectral content, i.e., characteristic absorption lines, in these longer wavelength regions that would allow one to be easily distinguished from another.

Terahertz radiation is not an ionizing radiation, so it does not have the potential to present health problems as would, for example, X-radiation (X-Rays). Terahertz radiation can be propagated for much longer distances in the atmosphere than X-rays, for example, several meters, and does not cause damage to electronic devices and unexposed film. In addition to offering a higher potential resolution in imaging than millimeter waves, terahertz radiation also offers a potential to provide sharper differentiation between different materials superimposed on one another and, accordingly provide higher contrast images than would be possible with millimeter waves.

It would be advantageous to exploit the imaging potential of terahertz radiation in security apparatus for examining luggage or packages for concealed objects or substances. Substances could include explosives, drugs, biological agents, and the like.

SUMMARY OF THE INVENTION

The present invention is directed to a method identifying a material of an object concealed in a package. In one aspect, the method comprises recording a plurality of images of the package and the object therein by detecting THz-radiation transmitted through the package. At least two of the images are recorded at different frequencies of said THz-radiation and at least two of the images are recorded at different transmission directions of the THz radiation. The absorption coefficient of an object at the different frequencies is estimated from the recorded images. The estimated absorption coefficients are compared with a table of known absorption coefficients of known materials to determine which of those materials may be the material of the object.

In one preferred embodiment only two images are recorded. One image is recorded at one transmission direction and one frequency and the image is recorded at another direction and another frequency.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the present invention.

DETAILED DESCRIPTION OF THE INVENTION

The object identification method of the present invention relies on the fact that the transparency (transmission) of many dielectric or organic materials to THz radiation decreases with both increasing density of the material and increasing frequency of the radiation. Accordingly, by determining the thickness of an object, and determining THz transmission of an object at two or more THz frequencies, an absorption coefficient of the object can be calculated at each of the different frequencies. The absorption coefficients so determined can be compared with catalog (look-up table) data of absorption coefficient versus frequency for various materials or various material densities to make an approximation of the density of the object. This can provide an indication of a material included in the object.

Figure 1:
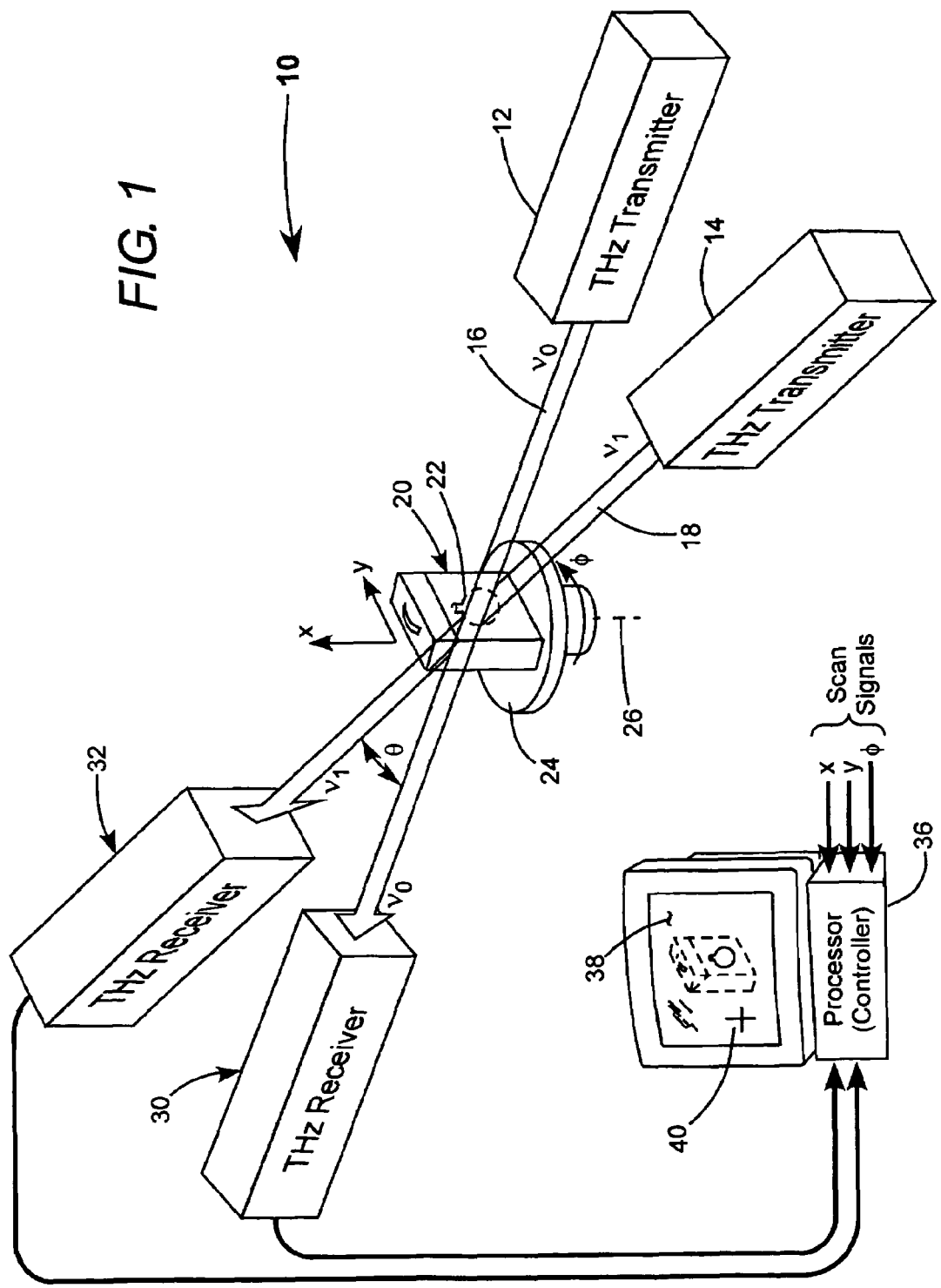
FIG. 1 schematically illustrates one preferred embodiment of a apparatus in accordance with the present invention for identifying materials in a non-metallic container, including two THz transmitters each transmitting beams of different THz frequency through the container at an angle to each other, two corresponding THz receivers for receiving the transmitted beams and a processor arranged to compare outputs of the two receivers to identify materials.

Referring now to the drawings, wherein like components are designated by like reference numerals, FIG. 1 schematically illustrates one preferred embodiment 10 of scanning THz imaging apparatus in accordance with the present invention for estimating the density an object concealed in a non-metallic package. In FIG. 1, and in other drawings referred to hereinbelow, the path of optical (THz) radiation is depicted by single-weight lines, either solid or dashed depending on frequency. The direction of propagation of the radiation is indicated by open arrowheads. Electronic connections are depicted by double-weight solid lines with the direction or directions of electronic communication indicated, where appropriate, by one or more solid arrowheads.

Apparatus 10 includes THz radiation transmitters 12 and 14. Transmitter 12 delivers a beam 16 of THz radiation 16 at a frequency $v_0$. Transmitter 14 delivers a beam 18 of THz radiation at a frequency $v_1$, different from frequency $v_0$. A package 20 to be examined, here containing a volume 22 of interest (an object) is placed on a platform 24, which is rotatable about an axis 26 as indicated by arrow $\phi$. Beams 16 and 18 are directed at an angle $\theta$ to each other such that the beams intersect within package 24. Angle $\theta$ is preferably between about 5° and 180°. Provision is made to scan package 20 with respect to beams 16 and 18 in orthogonal x and y-axes. This can be achieved by scanning beams 16 and 18 over a fixed position of the package, or by scanning the package, i.e., platform 24 with respect to fixed directions of the beams.

Beams 16 and 18 are intercepted by THz receivers 30 and 32 respectively after being transmitted through package 20. The output of each of the THz receivers 30 and 32 is connected to a processor (controller) 36. Scan signals representative of the x, y, and $\phi$ positions of the beams with respect to the package are also transmitted to the processor. This allows two two-dimensional electronic "images", one at each of the THz frequencies, to be captured by the processor, each image comprising values of transmission T (brightness) as a function of x and y coordinates ($T_{v,\phi}(x,y)$) for a particular value of $\phi$.

Electronic images recorded in the processor may be displayed individually or as a composite (for example, a ratio of the two) on a display screen 38. As the two images are taken at different angles the composite image can be in effect "stereoscopic", i.e., providing some shape information on an object or objects therein.

In one example of operation of apparatus 10, a scan at the two different frequencies, with the images being taken at different angles, is performed to provide two different images of the entire package, from which can be constructed an overall ratio-image of the entire package. In any image, the outline of the package and the outlines of objects therein would be visible from density (absorption coefficient) discontinuities at edges of the package and the objects.

The distance in an object traversed by radiation at one of the frequencies can be simply determined from the image at the other frequency, and a knowledge of the angle between the beams forming the images. Providing an angle of 90° between the beams forming the images simplifies the thickness determination. The brightness of an object at each frequency can be estimated at one or more positions in the object. The absorption coefficient of the object at each frequency can then be estimated from the brightness and the thickness (distance traveled in the object) estimate.

If, for example, if was determined that an object had a thickness of about 10 millimeters (mm) and transmission of the object was about 71% at a frequency of 1.4 THz and 21% at a frequency of about 3.1 THz the object could be estimated to have absorption coefficients of 0.29 cm$^{-1}$ at 1.4 THz and 0.79 cm$^{-1}$ at 3.1 THz. If, in the look-up table, the two closest stored sets of absorption coefficient values 0.32 cm$^{-1}$ for a material A (density A) and 0.55 cm$^{-1}$ for a material B (density B) at the 1.4 THz frequency, and 0.81 cm$^{-1}$ for a material A and 0.91 cm$^{-1}$ for a material B at the 3.1 THz frequency, then it could be assumed that the object was more likely of material A than of material B.

Clearly a thickness estimate, i.e., an estimated of the distance traveled in the object by a beam, can be made if the images at different angles are taken at the same frequency. In this case, however, at least a third image must be recorded at another frequency to allow the absorption coefficient to be estimated at both frequencies.

Specific absorption coefficient ranges representing specific materials of interest may be identified by a color code or the like to aid recognition. If an object or volume of interest is identified in the initial "overall" image, the apparatus may be "zoomed-in" on the object by performing another scan within bounding x and y-coordinates of the volume of interest with the same number of scan steps but with shorter distances therebetween. The area to be zoomed can be defined by mouse-controlled movement of a cursor 40 or the like, around the overall image in display 38. Acquisition and zooming of the object area may also be done automatically by suitable programming of the image processing software. Further shape-information on an object may be obtained processing individual-frequency images or ratio-images at different values of $\phi$. Further shape-information and transmission on an object may also be obtained by arranging apparatus 10 such that angle between beams 16 and 18 can be varied and processing images taken at different values of $\theta$.

The above presented image processing schemes are but examples of schemes that may be used in apparatus in accordance with the present invention. One skilled in the image processing art, having appreciated principles of the present invention described herein, may devise other image processing or display methods for identifying objects or materials thereof without departing from the spirit and scope of the present invention. Those skilled in the art to which the present invention pertains will also recognize that while apparatus 10 is described as including only two THz transmitters providing two beams at two different frequencies, three or more THz transmitters may be arranged to provide three or more beams at three or more different frequencies. Provision of additional transmitters and different probe frequencies may provide an added degree of certainty in identification of materials, but at the expense of cost and complexity of the apparatus and the necessary image processing.

THz transmitters for apparatus 10 must most preferably deliver CW radiation at a power of at least about 1.0 milliwatts (mW). This is achievable with certain types of THz lasers. One preferred THz laser for the inventive method is an optically pumped THz-laser in which a gaseous gain-medium is pumped by radiation from a $CO_2$ laser. A THz-laser may have different nominal frequencies depending on the gaseous THz gain-medium. Any particular gain-medium has different discrete lasing frequencies about some nominal frequency characteristic of that gain-medium. Accordingly, it is possible to select output frequencies $v_0$ and $v_1$ from many different THz frequencies between about 0.3 THz and 10.0 THz, by selecting a particular gain-medium. Such $CO_2$ laser-pumped THz-lasers are commercially available. One such commercially-available THz-laser is a SIFIR-50 THz-laser available from Coherent Inc. of Santa Clara, Calif. This laser has excellent spatial mode quality and can emit between about 50 milliwatts (mW) and 100 mW of continuous wave (CW) power.

$CO_2$ laser-pumped THz lasers are preferred for apparatus 10 because of advantages including a wide range of available THz frequencies, relatively high power output, and reliability. Those skilled in the art, however, will recognize that, in theory at least, other THz radiation sources both laser and electronic may be used without departing from the spirit and scope of the present invention. By way of example, one possible electronic source of THz radiation is backward-wave oscillator. Such an oscillator can emit greater than 1.0 mW of CW power at (discrete) frequencies up to about 1.5 THz. THz backward-wave oscillators are at a less mature stage of development than THz-lasers and may not be as reliable as commercially available THz-lasers.

Other possible THz-lasers include Quantum cascade semiconductor lasers (QCL). These have an advantage of being relatively small by comparison with $CO_2$ laser-pumped THz lasers. Another advantage is that continuous tuning is possible over frequencies up to about 10 GHz. QCL lasers, however, must be operated at liquid Helium temperatures in order to achieve milliwatts of power output. In room temperature operation, output power is presently limited to only a few nanowatts (nW).

One THz source that is not suitable for use in the present invention is a laser-triggered gallium arsenide (GaAs) photomixer. While such a source can provide radiation over the entire THz range and accordingly be used to generate an entire THz spectrum of a material, output power is limited to tens of nanowatts which is too low to penetrate packages encountered in typical inspection situations.

Figure 2:
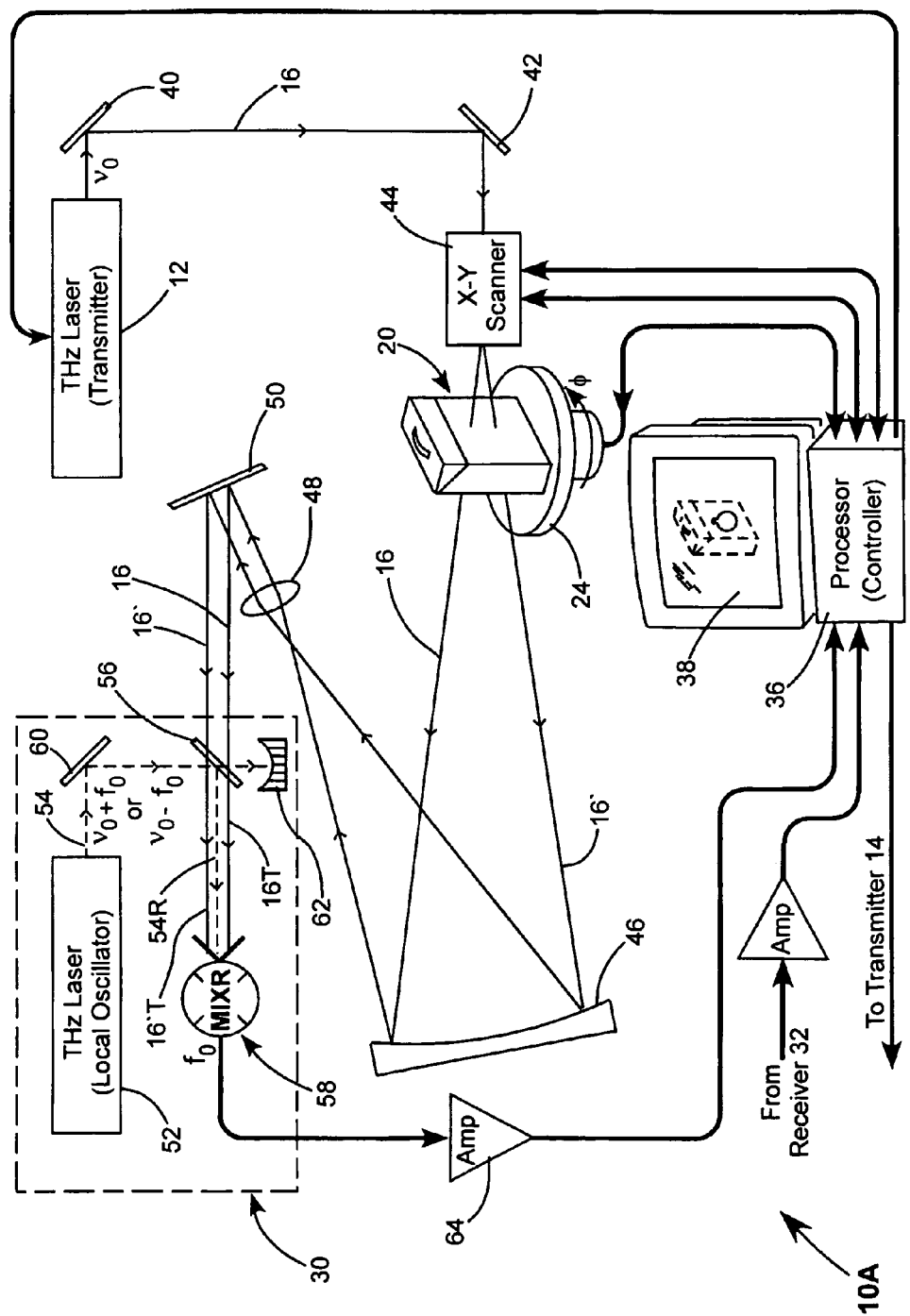
FIG. 2 schematically illustrates one preferred example of a THz transmitter and a THz receiver in a preferred implementation of the apparatus of FIG. 1.

FIG. 2 schematically illustrates a preferred implementation 10A of apparatus 10 including a preferred example of transmitter and receiver scheme and a scanner. The scheme is described with reference to only one of the THz transmitters and the corresponding receiver, here, transmitter 12 and 30. One skilled in the art will recognize from the depiction of apparatus 10 in FIG. 1 how a similarly configured transmitter 14 and receiver 32 would be incorporated in the apparatus.

In the apparatus of FIG. 2, THz-radiation source (THz) 12 provides beam 16 (depicted here by only a single solid line) of THz radiation (a signal beam), having a frequency $v_0$. Beam 16 is directed by mirrors 40 and 42 to an x-y scanner 44. Scanner 44 scans the beam in a raster fashion in x and y-axes perpendicular to each other and perpendicular to the general direction of propagation of the beam or system axis. As two-axis beam scanners are well-known in the art, a detailed description of the scanner is not presented herein.

The beam from the scanner passes through package 20 at locations corresponding to the instant beam position. Extreme positions of the scanned beam are indicated by lines 16 and 16'. The scanned beam is incident on a concave mirror 46 and is reflected thereby to a lens 48. The mirror and the lens are configured and arranged such that the scanned beam leaves lens 48 in the same direction, whatever the instant scan angle in the total range of scan angles. After leaving lens 48 the scanned beam is directed by another mirror 50 into receiver 30.

Receiver 30 is a heterodyne receiver and includes a THz laser 52, which functions as a local oscillator (LO). A beam 54 of radiation from THz-laser 52 is required to have a frequency that is offset from the frequency $v_0$ of the signal beam 16 by a frequency $f_0$. Frequency $f_0$ is one preferred frequency of an electronic signal including image data that will be electronically processed to provide an image of package 20 being scanned including an object or objects therein For a frequency offset $f_0$ between about 0.5 MHz and 15.0 MHz, THz-lasers 12 and 52 preferably have the same gain medium with laser 12 having an output frequency $v_0$ near the peak of the gain curve and laser 14 electronically tuned to output radiation at a frequency $v_0+f_0$ or $v_0-f_0$ where these frequencies are frequencies of transitions of the gain medium adjacent the transition of peak gain. This frequency-offsetting method for gas lasers, and circuits therefor, are well known in the art and a detailed description thereof is not necessary for understanding principles of the present invention. A detailed description is included in U.S. patent application Ser. No. 11/085859, filed Mar. 22, 2005, assigned to the assignee of the present invention, and the complete disclosure of which is hereby incorporated by reference.

The gain-medium of a THz laser typically consists of larger heavy gas molecules, for example, methanol ($CH_3OH$) or difluoromethane ($CH_2F_2$). Because of this, there are many possible laser transitions for any gas, spectrally very closely spaced. Accordingly, values for $f_0$ using this frequency offsetting method are typically in the above referenced MHz range. For values of $f_0$ between about 500 MHz and 200 GHz, lasers 12 and 52 preferably have different gain-media.

Continuing with reference to FIG. 2, on entering receiver 30, signal beam 16 is transmitted through a beamsplitter 56 onto a THz-detector or mixer (MIXR) 58. Detector 58 is preferably a corner-cube mounted Schottky-diode detector. Such detectors are commercially available, for example, from Virginia Diode Inc. of Charlottesville, Va. Beam 54 from laser 52 is directed by a mirror 60 to beamsplitter 56. Beamsplitter 56 reflects a portion of beam 54 on detector 58. A transmitted portion of beam 54 is incident on a beam dump 62. Preferably beamsplitter 56 has a reflectivity less than 50% to maximize the portion of beam 16 that is incident on detector 58. For a given power in beam 16, the reflection of beamsplitter 56 for radiation in beam 54 having frequency $v_0 \pm f_0$ is selected to allow sufficient power to be incident on detector 58 to "swamp" out other noise sources of the detector.

The wave fronts of the portions of beams 16 and 54 (16T and 54R) incident on the detector are preferably aligned to be parallel. The diameter of the two beam portions are also preferably arranged to be equal. The beam portions, beam portion 54R having a frequency of either $v_0+f_0$ or $v_0-f_0$, and beam portion 16T having a frequency $v_0$ interfere on the surface of the detector to provide a signal from the detector having the offset frequency $f_0$. The signal varies in amplitude according to the instant intensity of transmitted beam portion 16T, which, in turn, is dependent on the transmission through package 20 at corresponding instant x and y-coordinates of beam 16. The x and y-coordinates are a function of time.

A signal generated by detector 58 is amplified by an amplifier 64. The amplified signal is supplied to processor/controller 54. Signals from scanner 44 representative of the instant x and y-coordinates of the scanner are also transmitted to the processor. Accordingly, the processor is able to generate a two-dimensional matrix of amplitude values that can be used in image processing as described above. Although not shown in FIG. 2, the arrangement of transmitter 14 and receiver 32 of may be configured in a similar manner to transmitter 12 and receiver 32. A separate x-y scanner would be required. Output of the Schottky diode-detector of receiver 32 would be communicated via another amplifier 66 to processor/controller 36.

Figure 3:
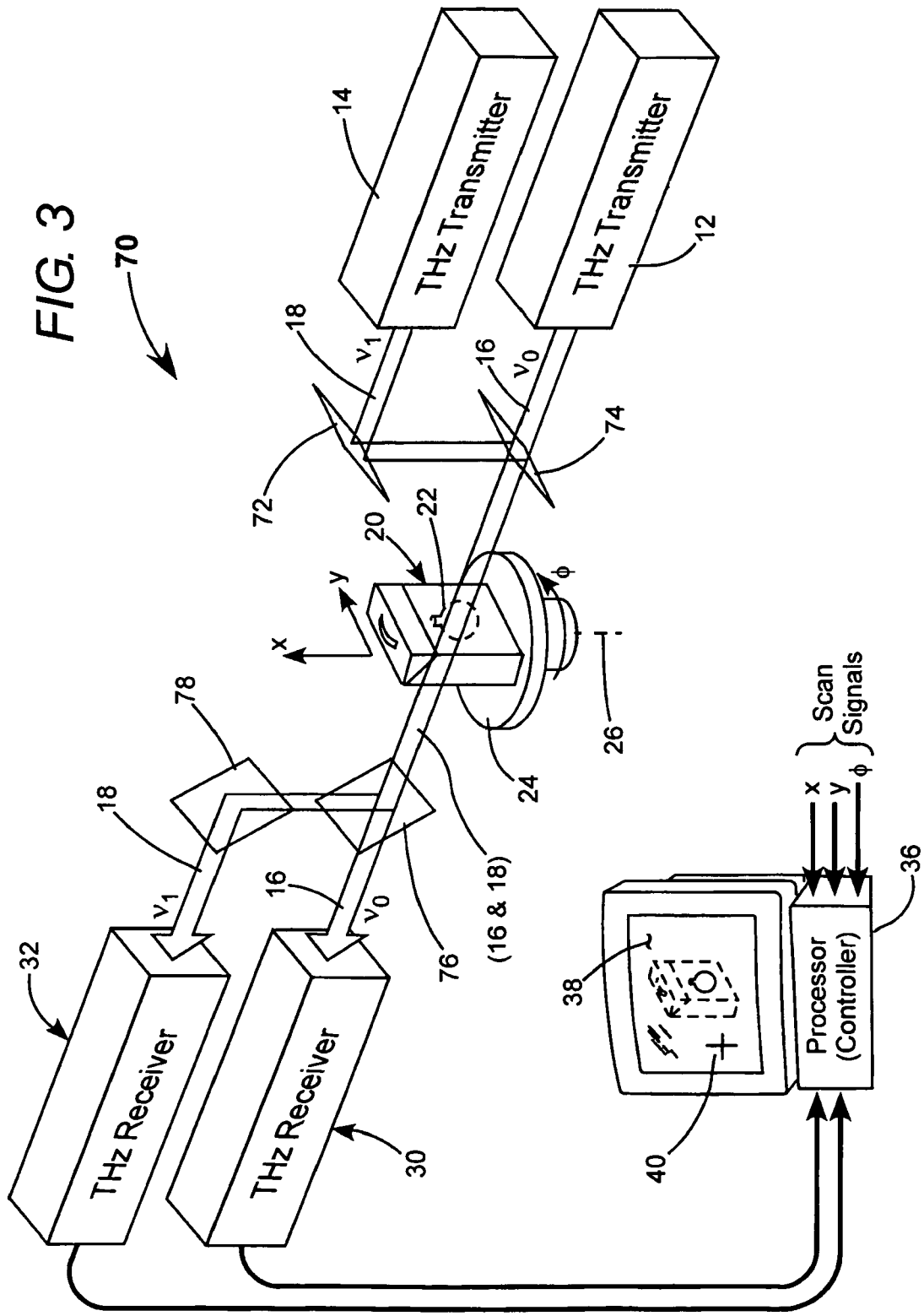
FIG. 3 schematically illustrates another preferred embodiment of a apparatus in accordance with the present invention for identifying materials in a non-metallic container, including two THz transmitters each transmitting beams of different THz frequency collinearly through the container, one diplexer for combining the two beams from the transmitters before the beams pass through the container, another diplexer for separating the two beams after the combined beams have passed through the container, two corresponding THz receivers for receiving the separated beams, and a processor arranged to compare outputs of the two receivers to identify materials.

In the foregoing description, the present invention is described in terms of directing the two THz beams at an angle to each other through a package being inspected. FIG. 3 schematically illustrates another preferred embodiment 70 of apparatus in accordance with the present invention similar to the apparatus of FIG. 1, but wherein the two THz-radiation beams are transmitted collinearly through the package and rotated simultaneously through a range of transmission directions. In apparatus 70 THz transmitters 12 and 14 are stacked one above the other. Beam 18 from transmitter 14 is directed by a turning mirror 72 to a frequency diplexer 74. Diplexer 72 is preferably a silicon (Si) etalon having a thickness selected such that, at the angles of incidence of beams 16 and 18 on the etalon (here, about 45°), there is a transmission peak (reflection minimum) at frequency $v_0$ and a transmission minimum (reflection maximum) at frequency $v_1$. Transmitters 12 and 14, turning mirror 74 and diplexer 76 are further arranged such that the beams transmitted and reflected by the diplexer proceed collinearly as a combined beam (16 & 18).

Beams 16 and 18 pass collinearly through the package 20 and are intercepted by another silicon frequency-diplexer 76. Diplexer 76 is configured similarly to diplexer 74, transmitting frequency $v_0$ and reflecting frequency $v_1$ and thereby separating beams 16 and 18 from the combined beam after the combined beam has passed. Separated beam 18 is directed by a turning mirror 78 to receiver 32.

Figure 4:
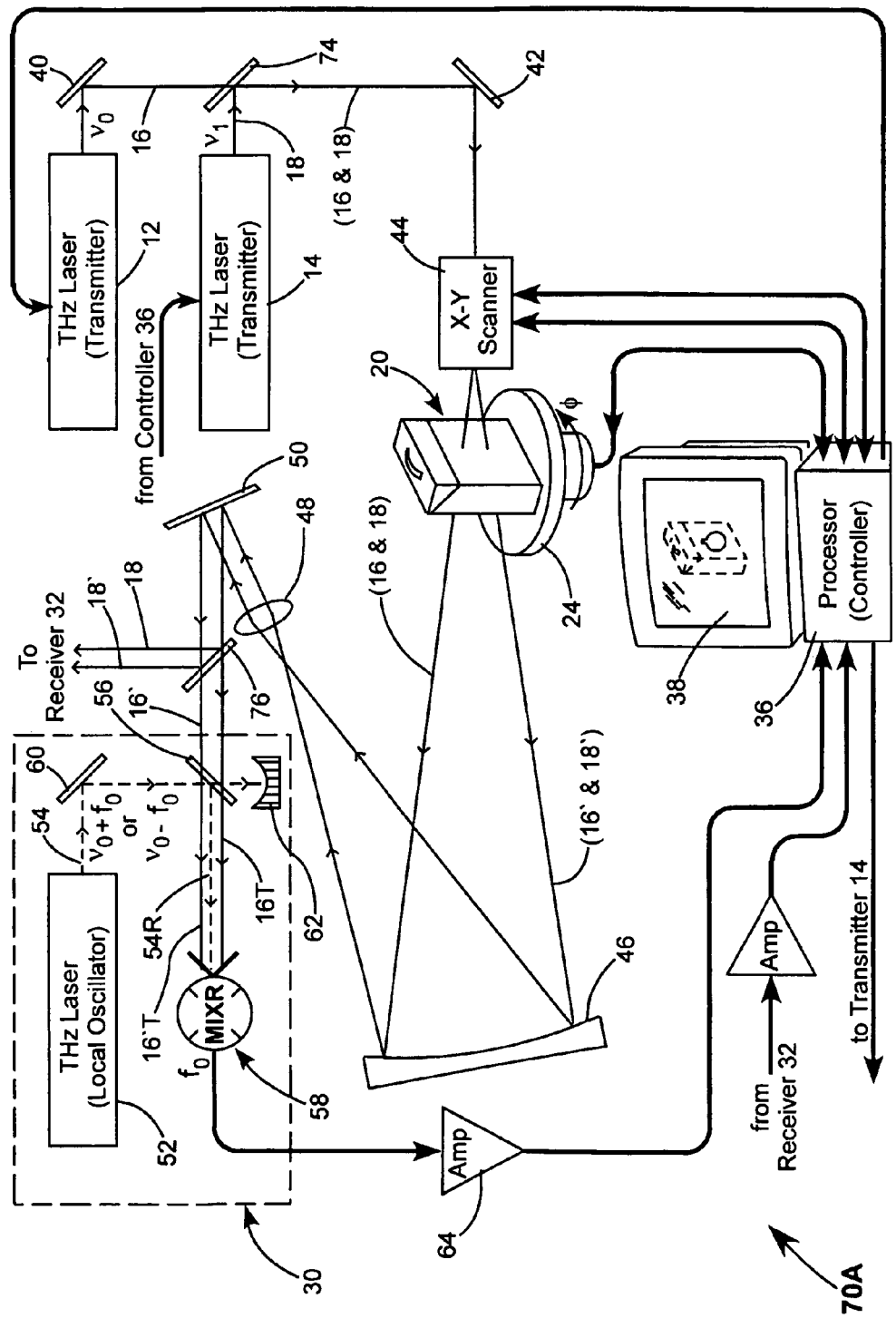
FIG. 4 schematically illustrates one preferred example of the two THz transmitters in a preferred implementation of the apparatus of FIG. 3 illustrating preferred locations for the combining and separating diplexers.

FIG. 4 schematically illustrates a preferred implementation 70A of the apparatus of FIG. 3. Apparatus 70A is similar to apparatus 10A of FIG. 2 with exceptions as follows. In apparatus 70A transmitter 14 is located below transmitter 12 diplexer 74 of FIG. 3 (transmissive for frequency $v_0$ and reflective for frequency $v_1$) is arranged such that beams 16 and 18 from transmitters 12 and 14 are combined collinearly into a single beam (16 & 18). It is this combined beam that is scanned by scanner 44. Extreme scan positions (angles) of the combined beam are designated 16 & 18, and 16' & 18'. These extreme scan positions are brought into proximity and made parallel to each other by lens 48 as described above with reference to FIG. 2. Diplexer 76 is located after turning mirror 50 and separates beams 18 and 18' from beams 16 and 16', with beams 18 and 18' being directed to receiver 32 (not shown). Locating the diplexer in this position provides that all positions if the scanned beams are incident at the same angle on the diplexer.

This collinear arrangement of the inventive apparatus has an potential advantage compared with the non-collinear apparatus of FIGS. 1 and 2, inasmuch as the two THz-beams have exactly the same path length in any object through which the beams pass. This can provide that detected difference in brightness (transmission) at the two frequencies are due primarily to the density of the object and the frequency difference. There are, however, potential disadvantages of the arrangement. One such potential disadvantage is that the above discussed opportunity for deriving shape information from two beams at an angle to each other and accordingly from two images simultaneously recorded. Shape information can still be obtained, however, from a series of images made sequentially over time at different values of φ as a result of the rotation of platform 24. A further potential disadvantage is that performance of receivers 30 and 32 may be adversely affected if separation of beams 16 and 18 from the combined beam by diplexer 76 is incomplete. This may be mitigated to some extent by electronic filtering in the receiver electronics or by additional optical filtering in paths of the separated beams.

In summary, the present invention provides a means for estimating the material composition of an object or material from images or transmission measurements of the object or material made at two different THz frequencies. The present invention is described above in terms of a preferred and other embodiments. The invention is not limited, however, to the embodiments described and depicted. Rather, the invention is limited only by the claims appended hereto.

What is claimed is:

1. A method of inspecting an object concealed in a package:
   scanning the package with a first beam of terahertz radiation at a first frequency;
   scanning the package with a second beam of terahertz radiation at a second frequency;
   recording a plurality of images of the package and the object therein by detecting THz-radiation transmitted through the package, at least one of the images being recorded at said first frequency of said THz-radiation and at least one of the images being recorded at said second frequency of said THz-radiation and at least two of the images being recorded at different transmission directions of the THz radiation; and
   estimating the absorption coefficient of object at the different frequencies from the recorded images.

2. The method of claim 1, wherein only first and second images are recorded, said first image being recorded by detecting THz radiation transmitted through the package in a first direction and having said first frequency, said second image being recorded by detecting THz radiation transmitted through the package in a second direction and having said second frequency.

3. The method of claim 2, wherein said first and second directions are at an angle between about 5 degrees and 180 degrees to each other.

4. The method of claim 3, wherein said first and second directions are at about 90 degrees to each other.

5. The method of claim 1, further including the step of comparing the estimated absorption coefficients with a table of known absorption coefficients of known materials to determine a possible material of the object.

6. The method of claim 5, wherein said estimating of the absorption coefficients includes estimating from one of the images the distance traversed in the object by the THz-radiation forming the other image.

7. The method of claim 1, wherein said THz-radiation is CW radiation having a power of at least about 1.0 mW.

8. The apparatus of claim 7, wherein each of said first and second receivers includes a single THz-radiation detector and said each of said first and second optical arrangements includes a scanner arranged to transmit said THz-radiation through the package at a number of different positions, and wherein said electronic circuitry is cooperative with said scanners and said receivers such a said image is recorded by recording a plurality of transmission values of said transmitted THz-radiation detected by said detectors at corresponding plurality of transmission positions.

9. Apparatus for inspecting a package, comprising:
   first and second sources of THz-radiation, said first and second sources delivering said THz-radiation at respectively first and second frequencies;
   first and second optical arrangements for transmitting said THz radiation from respectively said first and second sources thereof through the package;
   first and second THz-radiation receivers;
   third and fourth optical arrangement optical arrangements for collecting THz radiation transmitted through the package from respectively said first and second sources of THz-radiation, and delivering said collected radiation to respectively said first and second receivers; and
   electronic circuitry cooperative with said first and second THz-radiation receivers for recording electronic images of the package at each of said first and second frequencies and arranged to estimate from said images the absorption coefficient at each of said first and second frequencies of any object contained in the package.

10. The apparatus of claim 9, wherein said first and second optical arrangements transmit said THz-radiation from said first and second sources thereof through the package in respectively first and second directions at an angle to each other.

11. The apparatus of claim 9, further including a platform for supporting the package, said platform being selectively rotatable such that said THz-radiation from said first and second sources may be transmitted through the package in selectively variable directions.

12. The apparatus of claim 9, wherein said first and second optical arrangements are configured such that said THz radiation from said first and second sources thereof is transmitted collinearly through the package.

13. The apparatus of claim 9, wherein said electronic circuitry includes and an electronically stored table of absorption coefficients of a plurality of materials at said first and second frequencies and is further arranged to compare the estimated absorption coefficients of the material with the stored absorption coefficients and, from the comparison, to determine which one or more of the materials of the table may be included in the object.

14. The apparatus of claim 9, wherein each of said first and second THz-radiation sources delivers CW THz-radiation at a power of at least about 1.0 milliwatts.

15. A method of inspecting a package comprising the steps of:
scanning the package with a first beam of terahertz radiation at a first frequency;
scanning the package with a second beam of terahertz radiation at a second frequency, with the direction of the scanning of the second beam being different from the direction of scanning of the first beam;
detecting the first and second beams after transmission through the sample and generating output signals in response thereto; and
processing the output signals to estimate the absorption coefficient of material inside the package.

16. A method as recited in claim 15, further including the step of generating images of the package using the output signals.

17. A method as recited in claim 15, wherein the steps of scanning the package with the first and second beams of terahertz radiation are performed simultaneously.

18. A method of inspecting a package comprising the steps of:
scanning the package with a first beam of terahertz radiation at a first frequency from a first terahertz source;
scanning the package with a second beam of terahertz radiation at a second frequency from a second terahertz source with the direction of the scanning of the second beam being different from the direction of scanning of the first beam;
rotating the package with respect to the propagation direction of the first and second beams;
detecting the first and second beams after transmission through the sample and generating output signals in response thereto; and
processing the output signals to estimate the absorption coefficient of material inside the package.

19. A method as recited in claim 18, further including the step of generating images of the package using the output signals.

20. A method as recited in claim 18, wherein the steps of scanning the package with the first and second beams of terahertz radiation are performed simultaneously.

* * * * *